United States Patent
Nagai et al.

[19]

[11] Patent Number: 5,969,223
[45] Date of Patent: Oct. 19, 1999

[54] GAS SENSOR PACKAGE

[75] Inventors: Yuko Nagai; Tetsushi Sekiguchi; Tetsuya Makino; Michihiro Nakamura, all of Tokyo, Japan

[73] Assignee: Nihon Kohden Corporation, Tokyo, Japan

[21] Appl. No.: 09/109,093

[22] Filed: Jul. 2, 1998

[30] Foreign Application Priority Data

Jul. 2, 1997 [JP] Japan ................................ 9-176794

[51] Int. Cl.⁶ .................................................. G01D 18/00
[52] U.S. Cl. ..................... 73/1.06; 73/23.2; 206/213.1; 206/569; 206/305
[58] Field of Search .................... 73/1.06, 1.07, 73/1.04, 1.02, 23.2; 206/213.1, 569, 305; 436/9

[56] References Cited

U.S. PATENT DOCUMENTS

3,824,157  7/1974  Macur .
4,689,308  8/1987  Gerhard ..................................... 436/18
5,346,604  9/1994  Van Sin et al. .
5,780,302  7/1998  Conlon et al. ............................... 436/8

Primary Examiner—Michael Brock
Attorney, Agent, or Firm—Sughrue, Mion, Zinn, Macpeak & Seas, PLLC

[57] ABSTRACT

A gas sensor 1 has a catheter 3 to which a gas sensor body 4 and a signal guide member 5 for guiding a detection signal of the gas sensor body 4 are attached. The other end of the signal guide member 5 is connected to a connector 6. The gas sensor 1 is airtightly received in the reception body in the state where a connection terminal of the connector 6 is exposed to the outside. The reception body 2 is filled with a mixed gas containing a gas to be measured by a predetermined concentration. At the time of calibration, the connection terminal of the connector 6 is connected to a measurement amplifier while the reception body 2 is not opened and calibration is performed, and at the time of measurement, the reception body 2 is opened and the gas sensor 1 is taken out to perform ordinary measurement.

9 Claims, 7 Drawing Sheets

GAS SENSOR PACKAGE

BACKGROUND OF THE INVENTION

1. Field of the Invention

The present invention relates to a gas sensor package which receives a gas sensor having a gas sensor body to be arranged at a measurement position, a signal guide member for leading a detection signal of the gas sensor body to another means, and a connector attached to a top end of the signal guide member.

2. Related Art

Conventionally, calibration of a gas sensor of this kind was performed in a condition that a gas sensor body was immersed in a calibration liquid which was received in an ampoule and which was available on the market.

In the case of performing such calibration, however, there was a defect that the work was troublesome and it was necessary to take a gas sensor out of a package at the time of calibration, so that the gas sensor could not be kept clean till the time of actual measurement. There was another defect that if calibration was performed in a condition that a gas sensor body was immersed in a calibration liquid, it took a long time before a detection signal became stabilized.

SUMMARY OF THE INVENTION

An object of the present invention is to make it possible to perform calibration of a gas sensor easily and rapidly in the state that the gas sensor is kept clean.

According to the present invention, there is provided a gas sensor package for receiving a gas sensor having a gas sensor body, a signal guide member connected at its one end to the gas sensor body to lead a detection signal of the gas sensor body, and a connector connected to the other end of the signal guide member, a reception body for receiving at least the gas sensor body and for airtightly receiving the gas sensor in a state where at least a connection terminal of the connector is exposed to the outside, and an atmosphere filled in the reception body and containing a gas to be measured at a predetermined concentration.

In the case of using the gas sensor received in this package, an operator connects the connection terminal of the connector to a measurement amplifier and performs calibration before the operator opens the reception body. At this time, the concentration of a gas to be measured in the inside of the reception body is known and the operator adjusts the measurement amplifier so that the value displayed becomes this concentration value. Next, the operator opens the reception body and sets the gas sensor body at the measurement position to perform actual measurement.

According to the present invention, the connector of the gas sensor is constituted by a first connector having at its opposite ends connection terminals and a second connector separably connected to one of the connection terminals of the first connector, the first connector being fixed to the reception body in a state where the other connection terminal is exposed to the outside of the reception body.

In the connector having such a configuration, if the second connector is separated from the first connector and directly connected to a measurement amplifier after the reception body is opened, the gas sensor can be handled in condition that it is perfectly separated from the reception body.

According to the present invention, the gas sensor has a catheter, the gas sensor body being attached to the catheter, the whole of the catheter being received in the reception body.

In such a configuration, it is sufficient if the reception body is opened at the time of actual measurement, and hence the catheter can be held clean before the time of calibration.

According to the present invention, water and a water-holding material are received in the reception body.

In such a configuration, if the whole package is heated, high-pressure steam is generated in the inside of the reception body to thereby heighten the sterilization effect of the gas sensor. The water is held by the water-holding material at room temperature.

According to the present invention, the reception body is provided with a connector holding member for holding the connector and having a hole portion which makes the inside and outside of the reception body communicate each other, the connector being held in the connector holding member through screw-engagement between respective screw portions formed in a circumferential surface of the connector and a circumferential wall surface of the hole portion.

In such a configuration, if an operator rotates the connector to release screw-engagement between the screw portions after calibration, the connector is separated from the reception body.

DETAILED DESCRIPTION OF THE PREFERRED EMBODIMENTS

Figure 1:
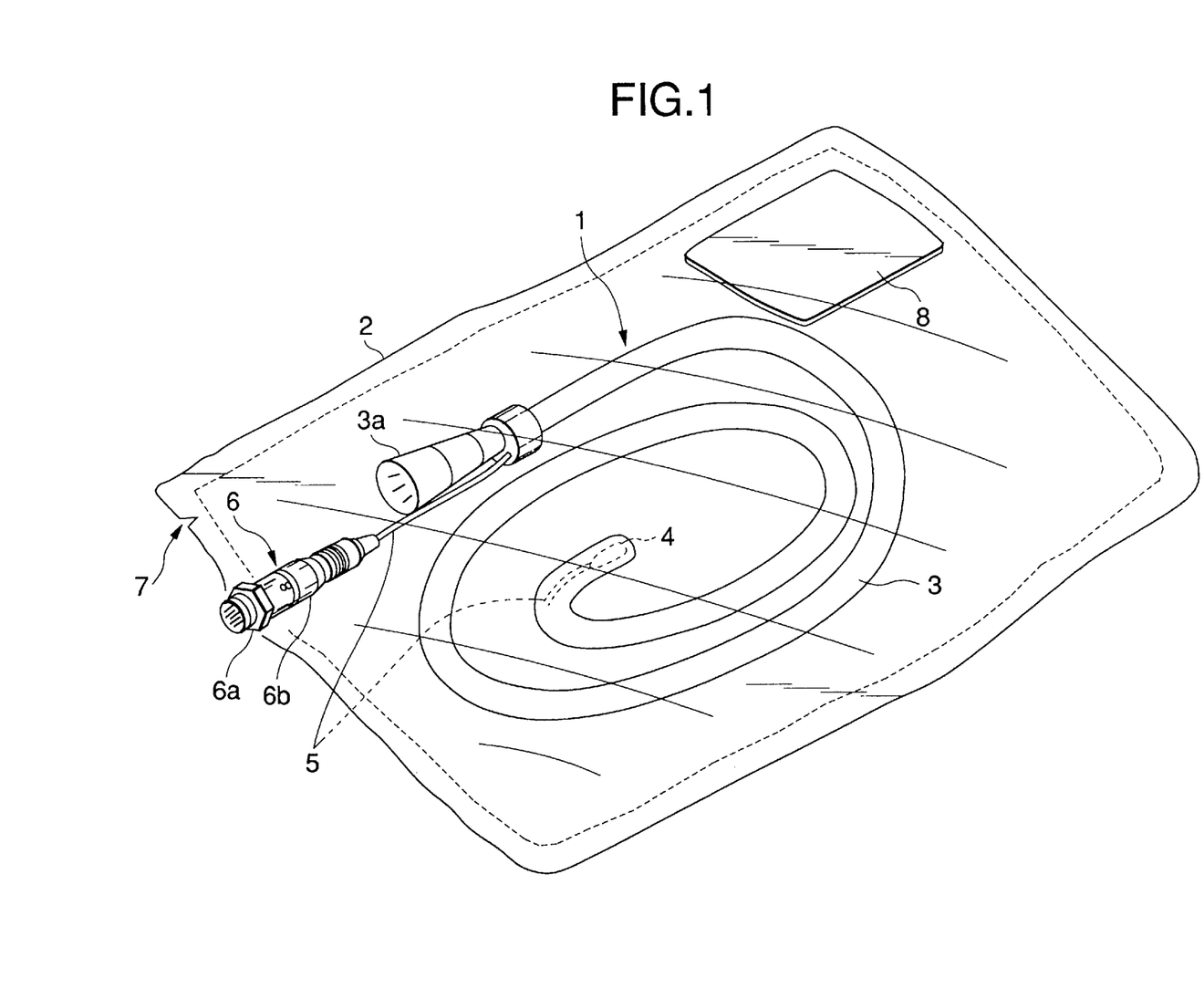
FIG. 1 is a perspective view showing the whole of a first mode for carrying out the present invention.
Figure 2:
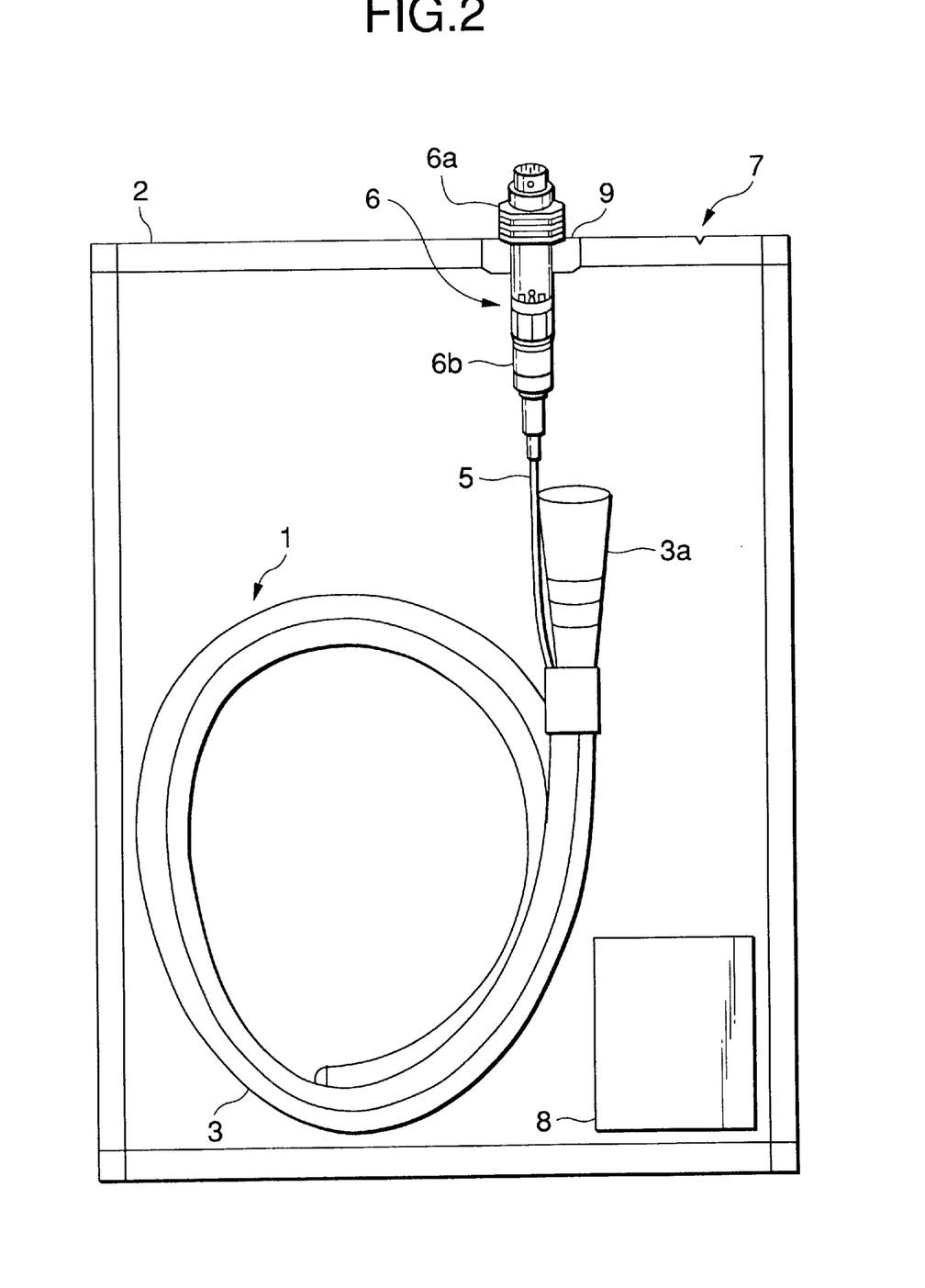
FIG. 2 is a plan showing the package shown in FIG. 1.

FIG. 1 is a perspective view showing a gas sensor package which is a first mode for carrying out the present invention, and FIG. 2 is a plan view of the same. As shown in the drawings, a gas sensor 1 is received in a reception body 2 (in the drawings, the reception body 2 is illustrated as a transparent member in which the inside is sufficiently visible). The gas sensor 1 has a catheter 3. The catheter 3 has a hole portion provided in the vicinity of a top end thereof so as to communicate with the outside and has a connecting portion 3a provided at the base portion thereof so that the connection portion 3a may be connected to another pipe for injecting a medicine liquid into the catheter 3 or for removing humor from the catheter 3.

A gas sensor body 4 is attached to the inside of the catheter 3 in the vicinity of its top end. As the gas sensor body 4, for example, an ion-sensitive field-effect transistor (ISFET), an optical-fiber-type gas sensor or a severinghaus-type electrode is used. A signal guide member 5 for guiding a detection signal of the gas sensor body 4 is connected at its one end to the gas sensor body 4, passed through the catheter 3, and then drown out to the outside from the base end of the catheter 3. The signal guide member includes the electric wire when the sensor sends out the electric signal the optical fiber when the sensor sends out the optical signal.

A connector 6 is attached to the other end of the signal guide member 5 so as to be connected to an external apparatus. The connector 6 is constituted by a first connector 6a having at its opposite end portions connection terminals, and a second connector 6b detachably connected to one of the connection terminals of the first connector 6a.

In the first connector 6a, the other connection terminal is exposed to the outside of the reception body 2, and the circumferential surface of the other connection terminal is tightly fixed with no clearance to the reception body 2 through a reinforcing member 9 as shown in FIG. 2.

The reception body 2 is formed of a pair of sheet-like members with their circumference bonded with each other. The sheet-like member may be any material so long as it has quality to prevent any gas from permeating therethrough. For example, it is preferable to use a laminated film using some of materials including, for example, polyester, aluminum, nylon, polypropylene, etc. One notched portion 7 is formed in the circumferential portion of the reception body 2. The gas sensor of this first mode is used for detecting a carbon dioxide gas, and the reception body 2 is filled with a mixed gas of a carbon dioxide gas and a nitrogen gas to an extent that the pressure thereof does not become negative or positive but it is substantially equal to the atmospheric pressure. Here, assuming that the ratio of occupation of the carbon dioxide gas to the whole is selected to be, for example, 5%. This value is printed on the surface of the reception body 2 or described in an operating manual accompanied to the gas sensor.

In the reception body 2, a small amount of water and a sponge body 8 are further received. The water is received for the purpose of generating high-pressure steam in the inside of the reception body 2 to thereby improve the sterilization effect, when the whole package is heated to sterilize the gas sensor 1 after completion of packaging. Further, the water is useful for preventing the gas sensor 1 from drying at room temperature and useful for making the pressure in the inside of the reception body equal to the same saturated steam pressure as that in a body at the time of calibration. The water at room temperature is held in the sponge body 8. As a result, waterdrops can be prevented from depositing on the gas sensor 1.

Figure 3:
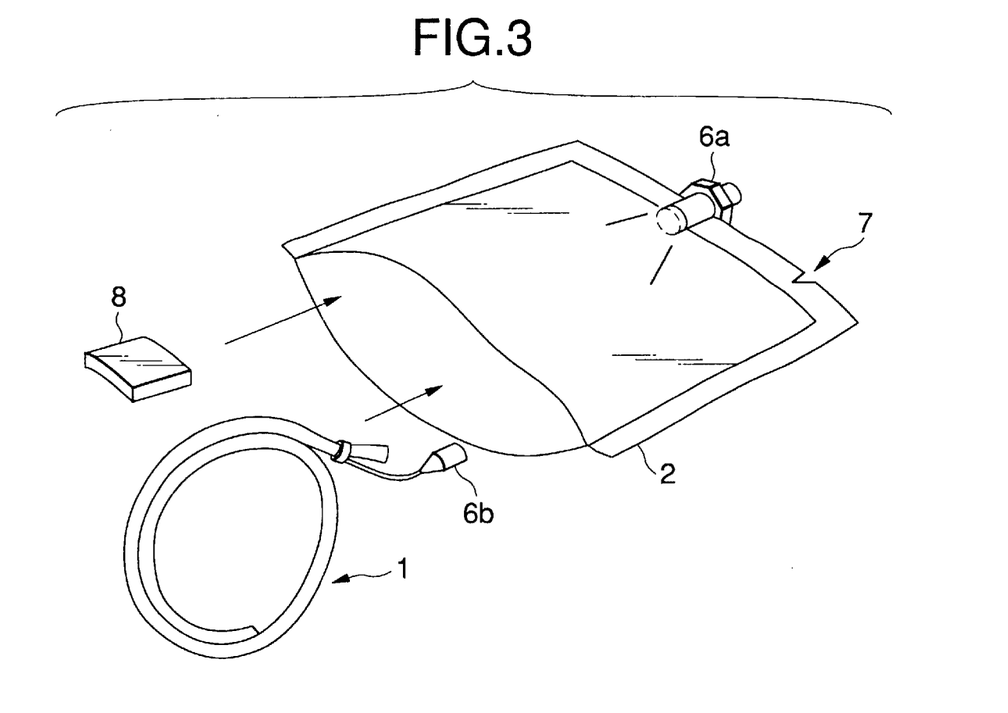
FIG. 3 is a view showing a first step of the package shown in FIG. 1.

Next, description will be made about steps till completion of such a package of the gas sensor 1. First, the bag-shaped reception body 2 having the opening portion and having the first connector 6a bonded in one place of a circumferential portion of the reception body 2, is produced as shown in FIG. 3. In this case, the first connector 6a is fixed to the circumferential portion of the reception portion 2 such that one and the other connection terminals of the first connector 6a are disposed inside and outside the reception body 2 respectively.

Next, the gas sensor 1 is put into the reception body 2 from the opening portion and the second connector 6b is connected to the first connector 6a. Further, the sponge body 8 containing water is put into the reception body 2.

Figure 4:
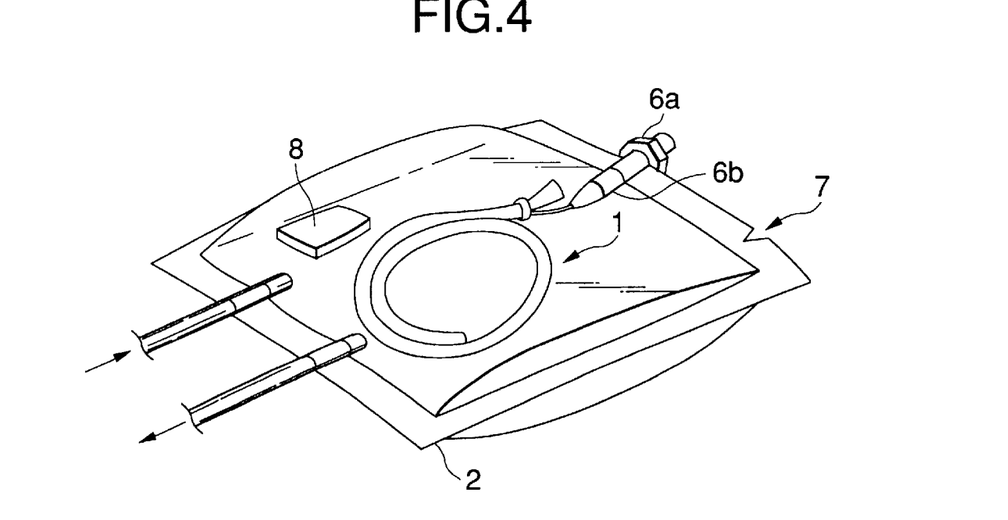
FIG. 4 is a view showing the next step of the package shown in FIG. 1.

Next, as shown in FIG. 4, the reception body 2 is filled with the above-mentioned calibrating gas and sealed by using a heat sealer machine having two nozzles so as to be able to fill and seal a gas.

Next, description will be made about a manner how to use the thus packaged gas sensor 1. First, an operator connects the first connector 6a to a measurement amplifier in the state where the package is not opened and performs calibration. The concentration of a carbon dioxide gas contained in the package is printed on the surface of the reception body 2 or described in the operating manual of the gas sensor 1 as described above. The operator adjusts the measurement amplifier so that this concentration, that is, 5% in this case, is displayed.

Next, the operator separates the first connector 6a from the measurement amplifier, opens the reception body 2 from its notched portion 7, separates the second connector 6b from the first connector 6a, and takes the gas sensor 1 out. Then, the operator inserts the gas sensor 1, for example, into the stomach of a patient from his/her nose so as to perform actual measurement.

Next, the operator connects the second connector 6b to the measurement amplifier to measure the concentration of the carbon dioxide gas.

In this mode, the configuration is made such that the connector 6 can be separated into the first and second connectors 6a and 6b, so that after calibration, the second connector 6b is directly connected to the measurement amplifier without through the first connector 6a, to thereby perform measurement. That is, the reception body 2 is disposed in the condition that the first connector 6a is attached to the reception body 2. Therefore, in packaging, the first connector 6a may be bonded to the reception body 2 freely without taking the later separating work of the first connector from the reception body into consideration. Further, in use of the gas sensor 1, it is not necessary to perform the separating work per se. In this mode, therefore, it is easy to perform the packaging work and to use the gas sensor taken out of the package.

Further, a calibration condition announcement member is employed to the connector so that the measurement amplifier automatically performs the calibration operation.

Figure 8:
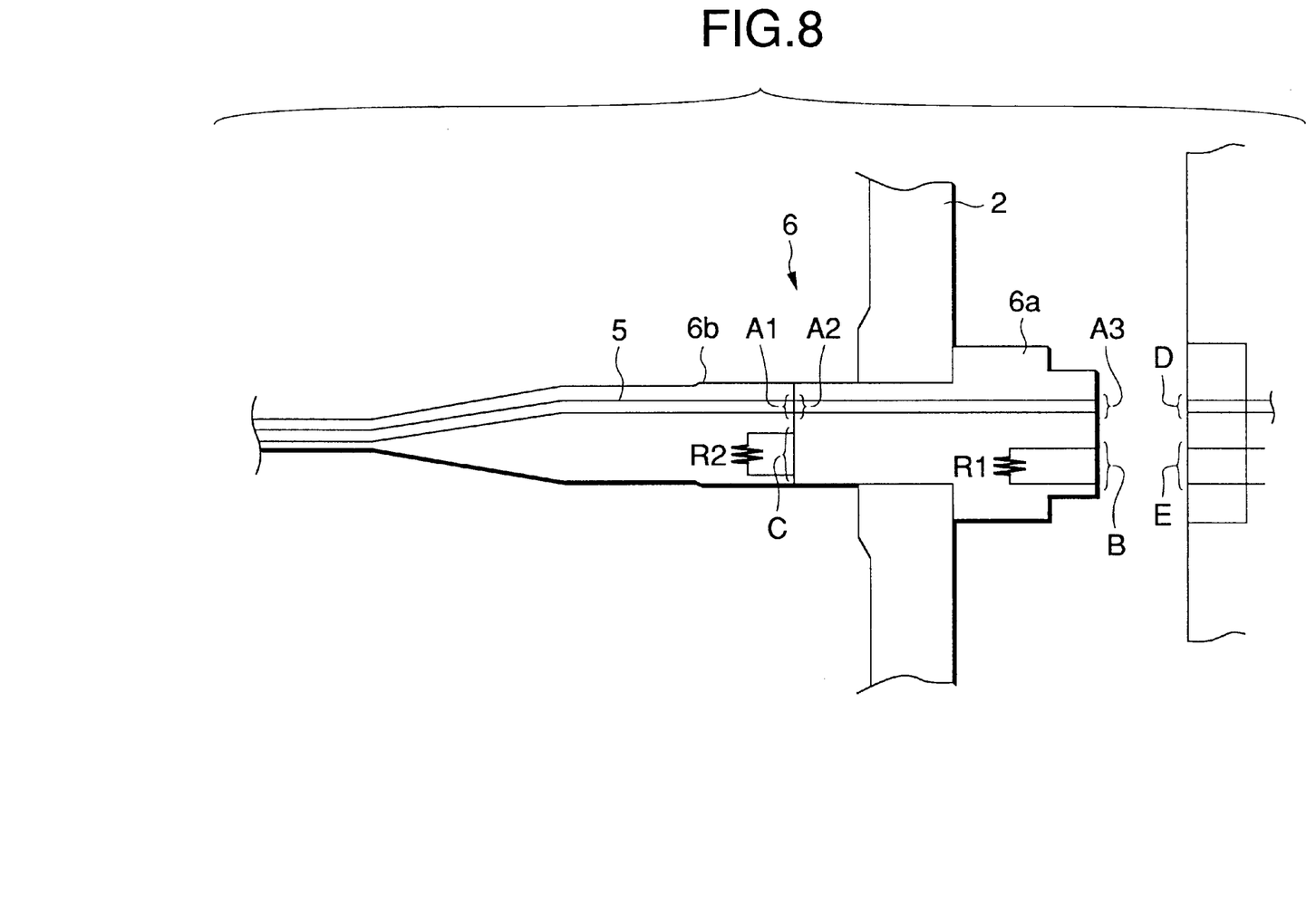
FIG. 8 is a view showing an arrangement of the connector of a modified embodiment of the present invention.

One embodiment as shown in FIG. 8 is described below.

The second connector 6b is provided with a detection signal output terminal A1 for introducing a detection signal from the gas sensor, and the first connector 6a is provided with a mating connector A2 received to the terminal A1 and a terminal A3, which is connected to the mating connector A2, for connecting the measurement amplifier. These structure is the same as the embodiment described above.

A resistor R1 and a resistor R2 having the different resistance value from each other are arranged into the first connector 6a and second connector 6b, respectively. The reason of employment of the resistors R1, R2 and the terminals B and C is to recognize the measurement amplifier receiving the first connector 6a or the second connector 6b. The calibration condition announcement member is consisted of the resistor R1 provided to the first connector 6a and the terminal B, in this embodiment.

On the other hand, the measurement amplifier contains terminals D and E. The terminal D is connected to the terminal A3 of the first connector 6a or the terminal A1 of the second connector 6b, and the terminal E is connected to the terminal B of the first connector 6a or the terminal C of the second connector 6b. Further, the measurement amplifier contains detecting means for detecting the connection of the resistor R1 or the resistor R2 in accordance with a signal passing through the terminal E and auto calibration means for determining an offset voltage of the amplifier when the detecting means detects the connection of the resistor R1.

Further, the measurement amplifier contains the function such that the auto calibration performs on the basis of the predetermined concentration of the carbon dioxide gas sealed in the reception body as a reference.

In this structure, the operator connects the first connector 6a with the measurement amplifier without the opening the package to perform the auto calibration by identifying the connection of the first connector 6a with the measurement amplifier.

Next, the operator opens the package to take the gas sensor and connects the second connector 6b with the measurement amplifier to obtain the measurement. At this time, the measurement amplifier recognizes the second connector 6b. Thus, it is not wrongly started to the calibration.

In this embodiment, if there is provided the structure such as the resistor R1 accommodated into the first connector 6a or the resistor R2 accommodated into the second connector 6b, it is possible to perform the auto calibration by identifying the connection of the first connector 6a with the measurement amplifier by the existence of the resistor. This structure is not limited by the resistance. It is capable for employing the open-circuit or the breakage of the wire.

Figure 9:
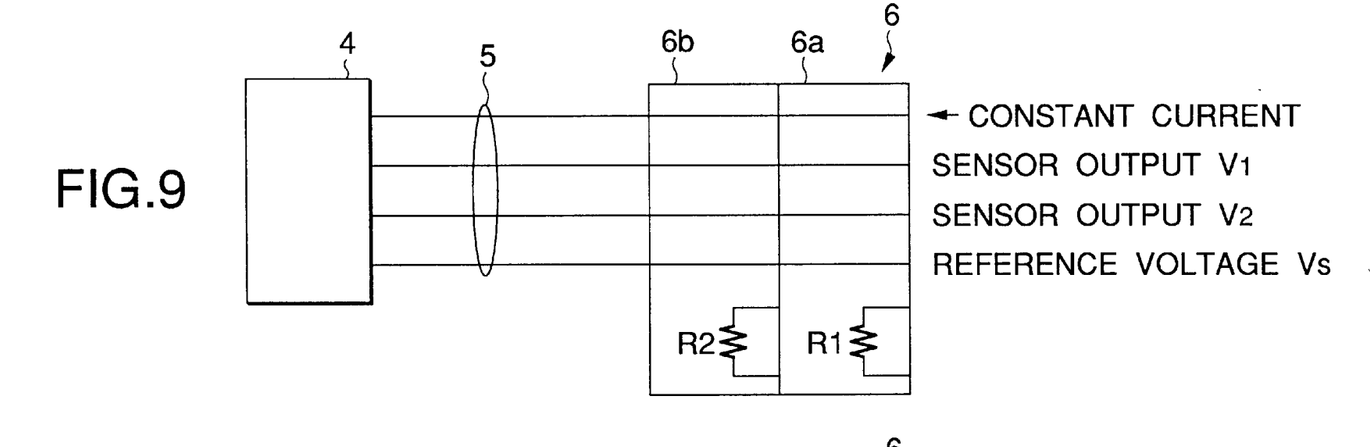
FIG. 9 is showing an actual circuit pattern when the sensor body employs ISFET type electrode.

As the embodiment described above, FIG. 9 shows an actual circuit pattern when the sensor body employs ISFET type electrode.

Figure 10:
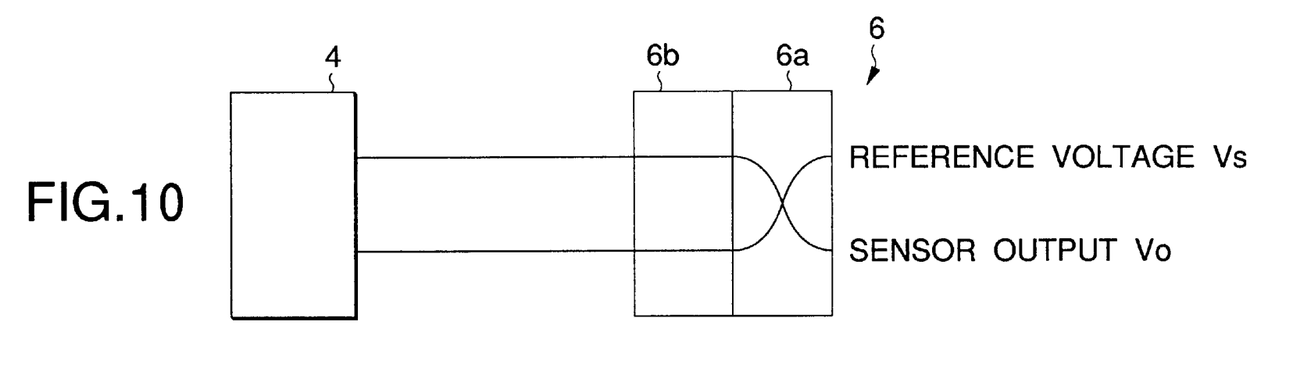
FIG. 10 is showing the auto calibration means accommodated into the connector when the sensor body employs the severinghaus-type electrode.

FIG. 10 shows the auto calibration means accommodated into the connector when the sensor body employs the severinghaus-type electrode. In this embodiment, the connector 6a and connector 6b do not have an electrode, and the line of the sensor output VO is switched with a reference voltage Vs in the first connector 6a.

In this structure, when the sensor body 4 is appeared into the gas to be measured, a direct voltage as several hundreds volts is detected so that the pole of the detection voltage is reversed of the existence of the first connector 6a. The measurement amplifier judges whether or not the auto calibration is performed.

According to this structure, it is capable for reducing the number of pins so that it is possible to minimize the connector and whole size of the package.

Figure 5:
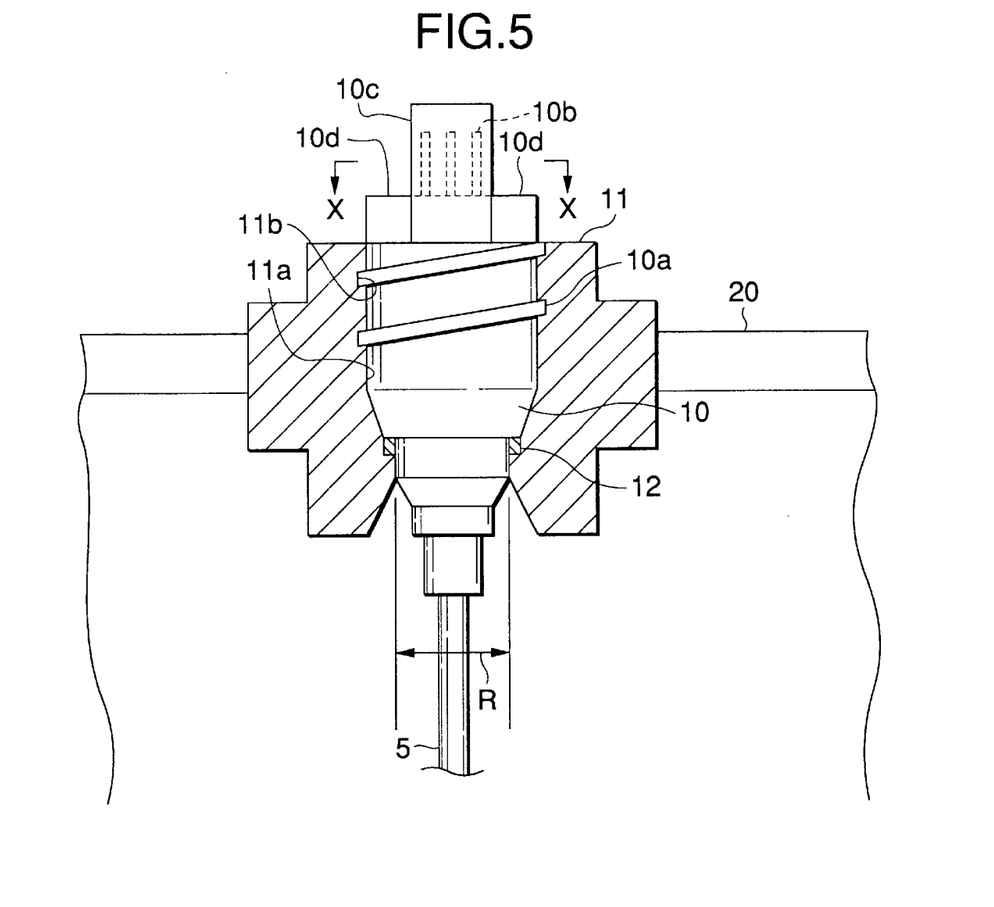
FIG. 5 is a view showing a main portion of a second mode for carrying out the present invention.

FIG. 5 shows a gas sensor package which is a second mode for carrying out the present invention. In this mode, a connector holding member 11 having a through hole 11a is attached to an reception body 20. It is a matter of course that the reception body 20 and the connector holding member 11 are bonded closely with each other without any clearance therebetween. A thread 10a is provided on a circumferential surface of a connector 10 and a screw groove 11b corresponding to the thread 10a is provided in a circumferential wall surface of the through hole 11a of the connector holding member 11. The connector 10 is fixed in the connector holding member 11 by screw-engagement between the thread 10a and the screw groove 11b. Here, the thread 10a and the screw groove 11b are formed such that the connector 10 can be separated from the connector holding member 11 if the connector 10 is rotated by one revolution. The outer diameter of the connector 10 is gradually reduced toward a signal guide member 5 by tapered or stage portions. A stage portion is formed in the connector holding member 11 in the vicinity of an outlet of the hole portion 11a in the inside of the reception body 20, and a ring-like packing 12 is provided in the stage portion so as to be pressed by the connector 10. As a result, the airtight property of the reception body 20 is kept high.

Figure 6:
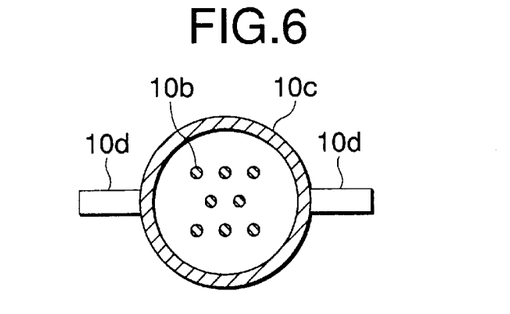
FIG. 6 is a sectional view take along line X—X in FIG. 5.

FIG. 6 is a cross section taken along line X—X in FIG. 5. As shown in the drawing, a pair of knobs 10d formed of plate-like members are provided on a base end of a guide pipe 10c of a connection terminal 10b of the connector 10. The quality and shape of the reception body 20 are the same as those of the package described in FIGS. 1 and 2. Any notched portion, however, is not required to be formed in this reception body 20. Further, a gas sensor to be received in the package is the same as that shown in FIGS. 1 and 2 and a gas to be filled into the reception body 20 is the same as that shown above.

In the case of making the package of the second mode, first, the reception body 20 having the opening portion and the connector holding member 11 attached thereto is prepared, and the gas sensor is inserted into and received in the reception body 20 from the through hole 11a of the connector holding member 11. Therefore, the minimum diameter R of the through hole 11a is set to such a size that the gas sensor can be taken in and out. In this case, the gas sensor has a catheter and hence the diameter R is set to such a size that the gas sensor with the catheter can be taken in and out. Next, if the connector 10 is inserted into the through hole 11a and rotated by one revolution by holding the knobs 10d by hand, the thread 10a and the screw groove 11b are screw-engaged with each other so that the connector 10 is fixed in the connector holding member 11, and at the same time the packing 12 is pressed to thereby block the through hole 11a. In this state (also the sponge body containing water is received in the reception body 20), as shown in FIG. 4, the reception body 20 is filled with the gas and the opening portion of the reception body 20 is sealed.

Next, description will be made about a manner how to use the thus packaged gas sensor. Similarly to the first mode, an operator performs calibration in the state where the package is not opened.

Next, if the operator separates the connector 10 from a measurement amplifier and rotates the connector 10 by one revolution by holding the knobs 10d by hand in the direction opposite to the direction of rotation at the time of attachment, the operator can separate the connector 10 from the connector holding member 11, that is, from the reception body 20. Then, if the operator draws the gas sensor out of the through hole 11a, the gas sensor is perfectly separated from the reception body 20. Next, the operator inserts the gas sensor, for example, into the stomach of a patient from his/her nose, and connects the connector 10 to the measurement amplifier again so as to perform actual measurement.

In this mode, although the connector 10 is of the inseparable type, the connector can be easily separated from the reception body 20. Therefore, the configuration of the connector 10 can be simplified.

Figure 7:
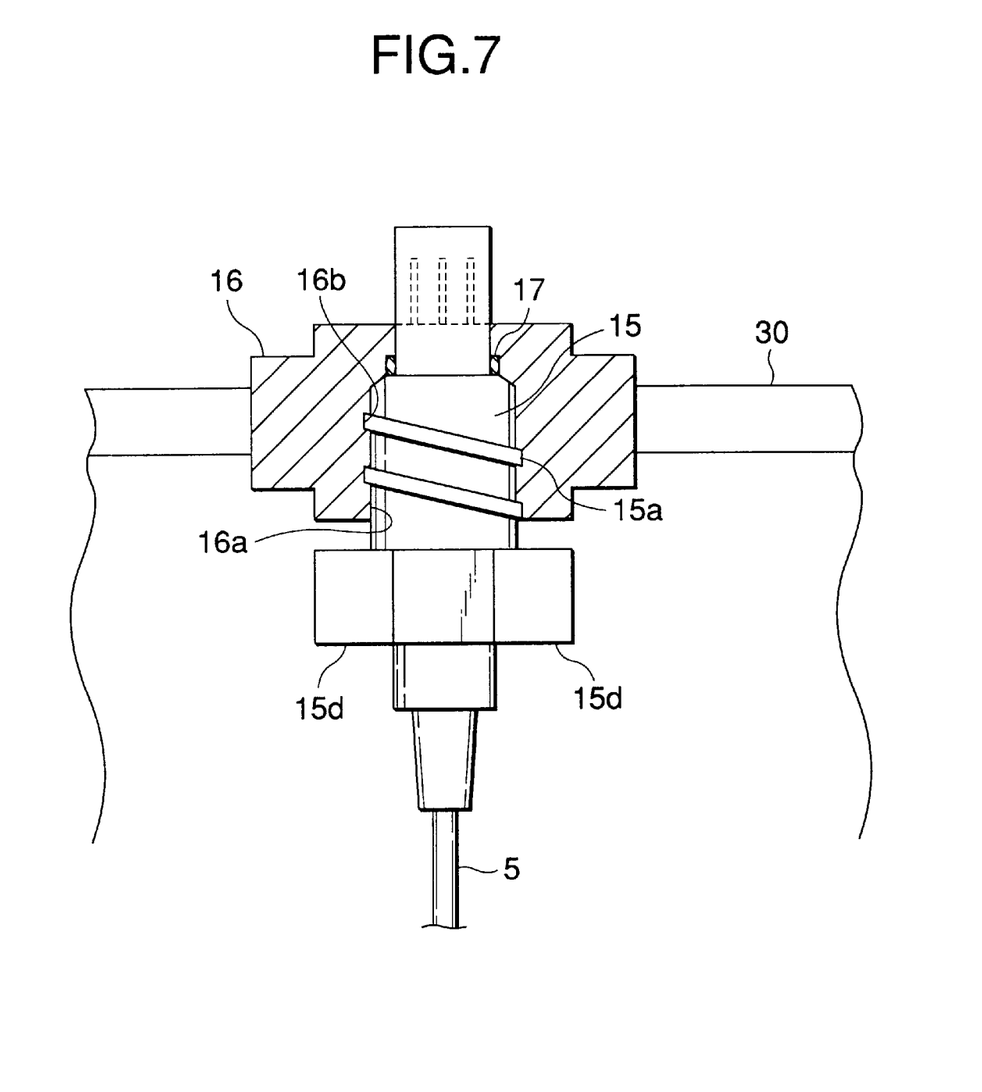
FIG. 7 is a view showing a main portion of a third mode for carrying out the present invention.

FIG. 7 shows a third mode for carrying out the present invention. The third mode is different from the second mode in that a connector 15 is attached/separated to/from a connector holding member 16 from the inside of a reception body 30. Therefore, knobs 15d for rotating the connector 15 are provided on the signal guide member 5 side so as to be disposed in the inside of the reception body 30. Similarly to the second mode, the connector 15 is fixed to the connector holding member 16 by screw-engagement between a thread 15a provided on a circumferential surface of the connector 15 and a screw groove 16b provided in a circumferential wall surface of a through hole 16a of the connector holding member 16. Further, similarly to the second mode, a ring-like packing 17 is provided on a stage portion formed in the connector holding member 16 and this ring-like packing 17 is pressed by the connector 15. Further, the quality and shape of the reception body 30, and a gas sensor to be received in the package are the same as those in the second mode. Moreover, a gas filled in the reception body 30 is the same as that in the second mode. A notched portion is however formed in the reception body 30.

In the case of making the package according to the third mode, first, the reception body 30 having the opening portion and the connector holding member 16 attached thereto is prepared and the gas sensor is received in the reception body 30. Differing from the second mode, however, this mode is convenient in that the gas sensor can be received from the opening portion of the reception body 30. Next, if the connector 15 is inserted into the through hole 16a and then rotated by one revolution by holding the knobs 15 by hand, the connector 15 is fixed in the connector holding member 16, and at the same time the packing 17 is pressed to block the through hole 16a. In this state (also the sponge body containing water is received in the reception body 30), as shown in FIG. 4, the reception body 30 is filled with the gas and the opening portion of the reception body 30 is sealed.

Next, description will be made about a manner how to use the thus packaged gas sensor. Similarly to the second mode, an operator performs calibration in the state where the package is not opened.

Next, the operator separates the connector 15 from a measurement amplifier, opens the reception body 30 from its notched portion, and rotates the connector 15 by one revolution by holding the knobs 15d by hand in the direction opposite to the direction of rotation at the time of attachment. As a result, the connector 15 can be separated from the connector holding member 16, that is, from the reception body 30. Then, if the operator draws the gas sensor out of the reception body 30, the gas sensor is perfectly separated from the reception body 30. The process thereafter is the same as that in the case of the second mode.

In this mode for carrying out the present invention, in the case of performing packaging, the gas sensor can be received in the reception body 30 through the opening portion which is not sealed yet, and hence the packaging work is easily performed. Further, after opening the reception body 30, the gas sensor can be taken out through the opening portion formed by opening the reception body 30, and hence taking-out of the gas sensor can be very easily performed.

Although the gas sensor to be received in the package according to any of the foregoing modes for carrying out the present invention is constituted by a catheter to which a gas sensor body, and so on, are attached, a gas sensor may be simply constituted by a gas sensor body, a signal guide member, and a connector with no catheter.

Although a carbon dioxide gas sensor is used in the foregoing modes, the same effects are obtained in the case of another gas sensor, for example, an oxygen gas sensor.

According to the present invention, calibration can be easily performed and it is not necessary to take the gas sensor out of the reception body at the time of calibration. Therefore, the gas sensor can be kept clean also at the time of calibration. Further, since at the time of calibration, the gas in the reception body has been already balanced with the gas sensor body, the response time is exceedingly short. Moreover, the gas hardly leaks to thereby change the concentration during calibration, so that calibration can be exceedingly accurately performed.

According to the present invention, if the second connector is separated from the first connector, and connected directly to the measurement amplifier after the reception body is opened, the gas sensor can be handled in a condition that it is quite separated from the reception body. Therefore, the gas sensor can be easily handled after opening the reception body. Further, since it is not necessary to consider separation of the first connector from the reception body after opening the reception body, no special method or means is required in bonding the first connector with the reception body. Therefore, the packaging work can be easily performed.

According to the present invention, the catheter can be kept clean before measurement is actually performed.

According to the present invention, if the whole reception body is heated, high-pressure steam is generated in the inside of the reception body to thereby make it possible to heighten the sterilization effects on the gas sensor. The water is held by a water holding material at room temperature and waterdrops are prevented from being attached onto the gas sensor. Further, the gas sensor is prevented from drying at room temperature. Moreover, by presence of this water, it is possible to provide the same saturated steam state as that in a body at the time of calibration.

According to the present invention, the connector can be easily separated from the reception body and hence the configuration of the connector can be simplified.

According to the present invention, before opening the package, the connector is connected to the measurement amplifier to send the signal for auto calibration to the measurement amplifier so that the operator is free from the calibration operation.

What is claimed is:

1. A gas sensor package comprising:
   a reception body for accommodating the gas sensor, said reception body being filled with a gas having a predetermined concentration in a seal condition; and
   a connector for transferring a signal from the sensor to guide it to an external portion of the reception body, the connector having a connection terminal exposed to the external portion of said reception body.

2. A gas sensor package as claimed in claim 1, wherein said reception body is made of a flexible material.

3. A gas sensor package as claimed in claim 1, further comprising:
   calibration announcement means for recognizing the calibration mode, said calibration means accommodated into the connector.

4. A gas sensor package for receiving a gas sensor comprising:
   a gas sensor body:
   a signal guide member connected at its one end to said gas sensor body to lead a detection signal of said gas sensor body;
   a connector connected to the other end of said signal guide member;
   a reception body for receiving at least said gas sensor body and for airtightly receiving said gas sensor in a state where at least a connection terminal of said connector is exposed to the outside, and
   an atmosphere filled in said reception body and containing a gas to be measured at a predetermined concentration.

5. A gas sensor package according to claim 4, wherein said connector of said gas sensor is constituted by a first connector having at its opposite ends connection terminals and a second connector detachably connected to one of said connection terminals of said first connector, said first connector being fixed to said reception body in a state where the other connection terminal is exposed to the outside of said reception body.

6. A gas sensor package according to claim 4, wherein said gas sensor has a catheter, said gas sensor body being attached to said catheter, the whole of said catheter being received in said reception body.

7. A gas sensor package according to claim 4 further comprising:

water and a water-holding material are received in said reception body.

8. A gas sensor package according to claim 4, wherein said reception body is provided with a connector holding member for holding said connector and having a hole portion which makes the inside and outside of said reception body communicate each other, said connector being held in said connector holding member through screw-engagement between respective screw portions formed in a circumferential surface of said connector and a circumferential wall surface of said hole portion.

9. A gas sensor package as claimed in claim 4, further comprising:

calibration condition announcement means for recognizing the calibration mode, said calibration means accommodated into the first connector.

* * * * *